(12) United States Patent
Koob et al.

(10) Patent No.: US 7,901,455 B2
(45) Date of Patent: Mar. 8, 2011

(54) TENDON OR LIGAMENT BIOPROSTHESES AND METHODS OF MAKING SAME

(75) Inventors: Thomas J. Koob, Tampa, FL (US); Douglas Pringle, Brandon, FL (US)

(73) Assignee: Shriners Hospitals for Children, Tampa, FL (US)

( * ) Notice: Subject to any disclaimer, the term of this patent is extended or adjusted under 35 U.S.C. 154(b) by 0 days.

(21) Appl. No.: 11/964,830

(22) Filed: Dec. 27, 2007

(65) Prior Publication Data

US 2008/0215150 A1    Sep. 4, 2008

Related U.S. Application Data

(60) Provisional application No. 60/882,065, filed on Dec. 27, 2006, provisional application No. 60/883,408, filed on Jan. 4, 2007, provisional application No. 60/890,660, filed on Feb. 20, 2007.

(51) Int. Cl.
*A61F 2/08* (2006.01)
*A61B 17/06* (2006.01)

(52) U.S. Cl. ............. 623/13.11; 623/13.14; 623/13.2; 206/63.3; 206/438

(58) Field of Classification Search ....... 623/13.11–13.2
See application file for complete search history.

(56) References Cited

U.S. PATENT DOCUMENTS

| | | | |
|---|---|---|---|
| 3,316,699 A | 5/1967 | Mattingly | |
| 4,590,928 A * | 5/1986 | Hunt et al. | 606/916 |
| 4,684,014 A * | 8/1987 | Davenport | 206/5.1 |
| 4,792,336 A * | 12/1988 | Hlavacek et al. | 623/13.18 |
| 4,841,962 A | 6/1989 | Berg et al. | |
| 4,883,486 A * | 11/1989 | Kapadia et al. | 623/13.15 |
| 4,979,956 A * | 12/1990 | Silvestrini | 623/13.11 |
| 5,078,744 A * | 1/1992 | Chvapil | 606/86 R |
| 5,106,949 A | 4/1992 | Kemp et al. | |
| 5,256,418 A | 10/1993 | Kemp et al. | |
| 5,263,984 A | 11/1993 | Li et al. | |
| 5,378,469 A | 1/1995 | Kemp et al. | |
| 5,656,605 A | 8/1997 | Hansson et al. | |
| 5,713,374 A | 2/1998 | Pachence et al. | 128/898 |
| 5,718,012 A | 2/1998 | Cavailaro | |
| 5,718,717 A | 2/1998 | Bonutti | |
| 6,090,117 A | 7/2000 | Shimizu | |
| 6,224,630 B1 | 5/2001 | Bao et al. | |
| 6,277,397 B1 | 8/2001 | Shimizu | |
| 6,280,474 B1 | 8/2001 | Cassidy et al. | |
| 6,292,697 B1 | 9/2001 | Roberts | |
| 6,335,007 B1 | 1/2002 | Shimizu et al. | |

(Continued)

FOREIGN PATENT DOCUMENTS

CA    2285161    4/2001

(Continued)

OTHER PUBLICATIONS

Nottage et al. "Arthoscopic Knot Tying Techniques." Arthroscopy: The Journal of Arthroscopic & Related Surgery 15(1999): 515-521.*

(Continued)

*Primary Examiner* — David Isabella
*Assistant Examiner* — Andrew Iwamaye
(74) *Attorney, Agent, or Firm* — Myers Bigel Sibley & Sajovec, P.A.

(57) ABSTRACT

The disclosure describes implantable bioprosthesis having an implantable construct with a multi-fiber array of collagen fibers attached together.

31 Claims, 8 Drawing Sheets

U.S. PATENT DOCUMENTS

| | | | |
|---|---|---|---|
| 6,395,029 B1* | 5/2002 | Levy | 623/11.11 |
| 6,531,147 B2 | 3/2003 | Sawhney et al. | |
| 6,565,960 B2* | 5/2003 | Koob et al. | 428/304.4 |
| 6,589,257 B1 | 7/2003 | Shimizu | |
| 6,592,623 B1 | 7/2003 | Bowlin et al. | |
| 6,645,247 B2 | 11/2003 | Ferree | |
| 6,692,528 B2 | 2/2004 | Ward et al. | |
| 6,713,537 B1 | 3/2004 | Ueda et al. | |
| 6,730,124 B2 | 5/2004 | Steiner | |
| 6,752,831 B2 | 6/2004 | Sybert et al. | |
| 6,821,530 B2 | 11/2004 | Koob et al. | |
| 6,936,072 B2 | 8/2005 | Lambrecht et al. | |
| 6,955,683 B2 | 10/2005 | Bonutti | |
| 7,084,082 B1 | 8/2006 | Shimizu | |
| 7,090,690 B2 | 8/2006 | Foerster et al. | |
| 7,115,146 B2 | 10/2006 | Boyer et al. | |
| 7,135,040 B2 | 11/2006 | Wang et al. | |
| 7,309,359 B2 | 12/2007 | Trieu et al. | |
| 7,354,627 B2 | 4/2008 | Pedrozo et al. | |
| 2001/0018619 A1* | 8/2001 | Enzerink et al. | 623/23.72 |
| 2002/0037940 A1 | 3/2002 | Koob et al. | |
| 2002/0123805 A1 | 9/2002 | Murray et al. | |
| 2003/0100108 A1 | 5/2003 | Altman et al. | |
| 2003/0230316 A1 | 12/2003 | Glucksman et al. | |
| 2004/0110439 A1 | 6/2004 | Chaikof et al. | |
| 2004/0131562 A1 | 7/2004 | Gower et al. | |
| 2004/0193241 A1 | 9/2004 | Stinson | |
| 2004/0224406 A1 | 11/2004 | Altman et al. | |
| 2004/0267362 A1* | 12/2004 | Hwang et al. | 623/13.15 |
| 2006/0095134 A1 | 5/2006 | Trieu et al. | |
| 2006/0257377 A1 | 11/2006 | Atala et al. | |
| 2006/0263417 A1 | 11/2006 | Lelkes et al. | |
| 2007/0118217 A1* | 5/2007 | Brulez et al. | 623/13.2 |
| 2007/0248643 A1 | 10/2007 | Devore et al. | |
| 2008/0020012 A1 | 1/2008 | Ju et al. | |
| 2008/0038352 A1 | 2/2008 | Simpson et al. | |
| 2008/0124371 A1 | 5/2008 | Turos et al. | |
| 2008/0161917 A1 | 7/2008 | Koob et al. | |
| 2008/0188933 A1 | 8/2008 | Koob et al. | |
| 2008/0200992 A1 | 8/2008 | Koob et al. | |
| 2009/0216233 A1 | 8/2009 | Wiedrich et al. | |
| 2009/0287308 A1 | 11/2009 | Davis et al. | |

FOREIGN PATENT DOCUMENTS

| | | |
|---|---|---|
| EP | 1493404 | 1/2005 |
| WO | WO 96/14095 | 5/1996 |
| WO | WO 01/72241 | 10/2001 |
| WO | WO 2008/041183 | 4/2008 |

OTHER PUBLICATIONS

Martin et al. "Anterior Cruciate Ligament Graft Preparation: A New and Quick Alternative to the Whipstitch." Arthroscopy: The Journal of Arthroscopic & Related Surgery. Online Publication Date of Nov. 29, 2006.*

Grog. "The Reef (Square) Knot." Animated Knots by Grog, downloaded at <http://www.animatedknots.com/reef/index.php> on May 28, 2009 using WayBack Machine on <www.archive.org> for publication date of Dec. 26, 2005.*

Moyer et al. "Arthroscopic Reconstruction of the Anterior Cruciate Ligament With Hamstring Tendons". Operative Techniques in Orthopaedics 2(1992):99-103.*

Grog. "The Reef (Square) Knot". Animated Knots by Grog, downloaded at <http://www.animatedknots.com/reef/index.php> on May 18, 2010 using WayBack Machine on <www.archive.org> for publication date of Dec. 26, 2005.*

International Search Report and Written Opinion for corresponding PCT application No. PCT/US2007/026365, Date of mailing Apr. 23, 2009.

Brunelli at al., Slip-knot flexor tendon suture in zone II allowing immediate mobilisation, The Hand, 1983, vol. 15, pp. 352-358.

Greis et al, The influence of tendon length and fit on the strength of the tendon-bone tunnel complex, Am. J. Sports Med., 2001, 29:493-497.

Becker et al., Early active motion following a beveled technique of flexor tendon repair: Report on fifty cases, Journal of Hand Surgery, 1979, vol. 4 No. 5, pp. 454-460.

Koob et al., Biomimetic approaches to tendon repair, Comp. Biochem. Physiol. A Mol. Integr. Phys., 2002, 133: 1171-1192.

Koob et al., Material properties of NDGA-collagen composite fibers: development of biologically based tendon constructs, Biomaterials, 2002, 23:202-212.

Koob et al., Mechanical and thermal properties of novel polymerized NDGA-gelatin hydrogels, Biomaterials, 2002, 24:1285-1292.

Messina, The double armed suture: Tendon repair with immediate mobilization of the fingers, Journal of Hand Surgery, 1992, 17A:137-142.

Powell et al., Forces transmitted along human flexor tendons during passive and active movements of the fingers, J. Hand Surg., 2004, 29:4:386-389.

Rodeo et al., Tendon healing in a bone tunnel. A biomechanical and histological study in a dog, J. Bone Joint Surg., 1993, 75:1795-1803.

Savage et al., Flexor tendon repair using a "six strand" method of repair and early active mobilisation, Journal of Hand Surgery, (British Volume,1989), 14B:396-399.

Silva et al., The insertion site of the canine flexor digitorum profundus tendon heals slowly following injury and suture repair, J. Orthop. Res., 2002, 20:447-453.

Trotter et al., Molecular structure and functional morphology of echinoderm collagen fibrils, Cell Tiss. Res., 1994, 275: 451-458.

Product advertisement, Conair QB3ECS Quick Braid Styling Kit, © 2007 (1 page)

Koob et al., Biocompatibility of NDGA-polymerized collagen fibers. I. Evaluation of cytotoxicity with tendon fibroblasts in vitro, © 2001 John Wiley & Sons, Inc.

Koob et al., Biocompatibility of NDGA-polymerized collagen fibers. II. Attachment, proliferation, and migration of tendon fibroblasts in vitro, © 2001 John Wiley & Sons, Inc.

Integra™ NeuraGen™ Nerve Guide, Product Broacher, 4 pages 2005.

Integra™ NeuraGen™ Nerve Guide, Product Webpage, http://www.integra-Is.com/products/?product=88, Date unknown but believed to be prior to the filing date of the present application, 2 pages.

Integra™ NeuraWrap™ Nerve Protector, Product Webpage, http://www.integra-Is.com/products/?product=198, Date unknown but believed to be prior to the filing date of the present application, 2 pages.

Whipknot product sheet, Smith & Nephew Endoscopy webpage: http://endo.smith-nephew.com/fr/node.asp?NodeID=3558, 2 pages, printed from website on Jun. 2, 2010 (Date of first publication unknown but for exam purposes only, is to be considered before the priority date of the instant application.).

Final Office Action for U.S. Appl. No. 11/964,756, mail date Mar. 26, 2010.

* cited by examiner

RESULTS FROM *In Vivo* TRIALS ON TENDON BIOPROSTHESIS
MECHANICS AT 3 AND 6 WEEKS
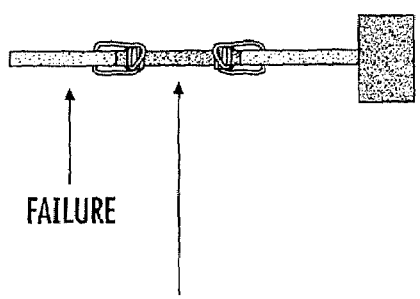
FIG. 7A
FAILURE
BIOPROSTHESIS NEVER FAILED
*in vivo* OR IN TENSILE TESTS
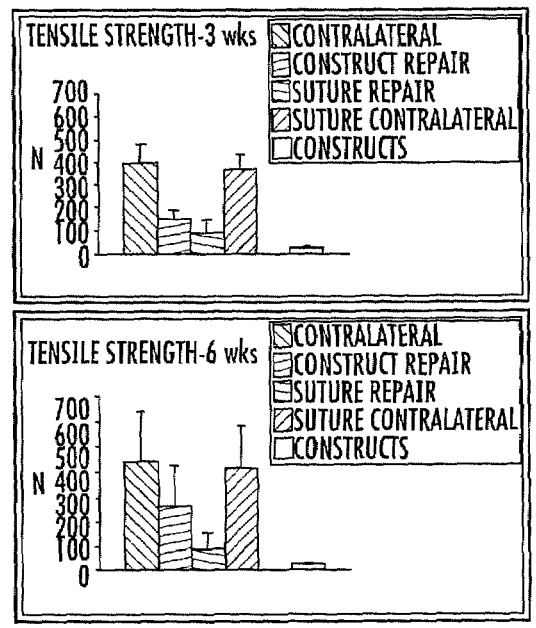
FIG. 7B
FIG. 7C
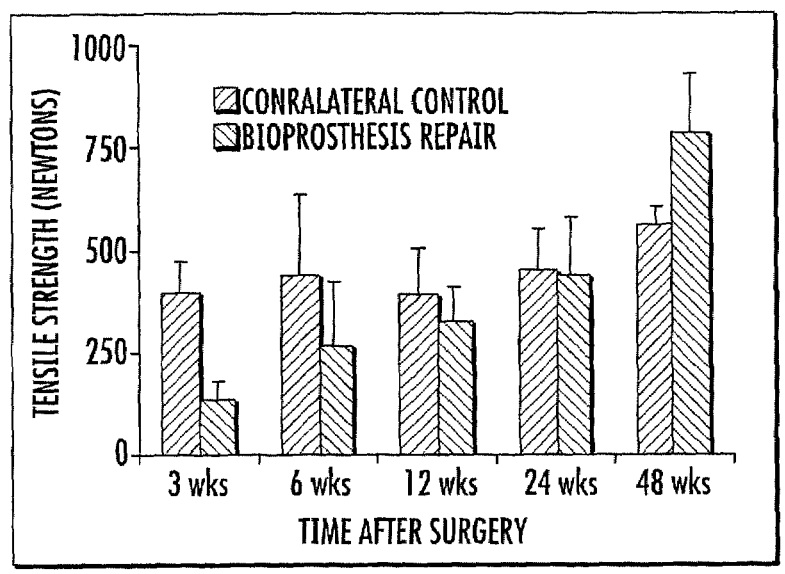
FIG. 7D

TENDON OR LIGAMENT BIOPROSTHESES AND METHODS OF MAKING SAME

RELATED APPLICATIONS

This application claims the benefit of priority to U.S. Provisional Application Ser. No. 60/882,065, filed Dec. 27, 2006, U.S. Provisional Application Ser. No. 60/883,408, filed Jan. 4, 2007, and U.S. Provisional Application No. 60/890,660, filed Feb. 20, 2007, the contents of which are hereby incorporated by reference as if recited in full herein.

FIELD OF THE INVENTION

The invention relates to implantable prostheses.

BACKGROUND OF THE INVENTION

It is believed that the linear organization of natural collagen fibers in tendons results in optimal stiffness and strength at low strains under tensile loads. However, this organization makes repairing ruptured or lacerated tendons difficult. Current suturing techniques to join split ends of tendons, while providing sufficient mechanical strength to prevent gapping, are often inadequate to carry normal loads and may not ever allow the tendon to regain original mechanical properties or mobility. Immobilization protocols used to restore tendon congruity may result in scar formation at the repair site and peripheral adhesions that can limit excursions. One or more similar issues may be associated with conventional ligament repair techniques.

SUMMARY OF EMBODIMENTS OF THE INVENTION

Embodiments of the present invention are directed to implantable biocompatible prostheses that provide new and alternative surgical treatments of tissue.

In some embodiments, the implantable bioprosthesis have a construct with a multi-fiber bundle or array, e.g., a plurality of fibers held together.

In some embodiments, the fibers can comprise nordihydroguairetic acid (NDGA) NDGA-treated polymer fibers. The construct may have a substantially flat configuration sized and configured to define a ligament bioprosthesis. In other embodiments, the construct may have a substantially circular cross-sectional shape sized and configured to define a tendon bioprosthesis.

Some embodiments are directed to implantable ligament or tendon bioprosthesis that include: (a) a flexible implantable biocompatible construct comprising polymerized collagen fibers having opposing first and second end portions; and (b) a first and second suture wrapped laterally at least once about a perimeter of a respective one of the first and second end portions of the construct and tied with a square knot, the suture having suture legs extending away from the square knot for affixing the construct to local bone or tissue.

In some embodiments, the fibers can be formed or arranged as an array of substantially parallel polymerized fibers. In some embodiments, the suture may be wrapped a second time around the respective end portion of the flexible construct and further tied with a pair of half-hitch knots that reside substantially symmetrically across from each other on opposing lateral sides of the construct so that pairs of the suture legs both extend axially away from the construct from an exit location that is laterally outside the bounds of the construct to attach to local tendon or ligament structure.

In particular embodiments, at least one of the sutures is wrapped a second and third time with respective second and third loops of the suture, and wherein each of the second and third loops ending with a two half hitch knots oriented to provide a desired exit configuration of the suture legs.

In some embodiments, the array of substantially parallel fibers comprise between about 15-57 elongate fibers compressed together so that adjacent fibers snugly contact each other to define the construct.

Some embodiments are directed to implantable ligament or tendon bioprostheses that include a flexible implantable biocompatible construct having a primary body comprising an array of substantially parallel polymerized collagen fibers having opposing first and second end portions, with at least one of the end portions merging into a braided segment of bundles of fibers defining the array.

Still other embodiments are directed to a medical kit for a tendon or ligament repair, augmentation or replacement. The kits include: (a) an implantable bioprosthesis construct having a primary body defined by an array of substantially parallel NDGA collagen fibers and having at least one suture attached to at least one end portion thereof; and (b) a sterile package sealably enclosing the collagen fiber construct with the at least one suture attached therein.

Still other embodiments are directed to methods of making a medical device. The methods include: (a) arranging a plurality of NDGA treated collagen fibers into a tendon or ligament prosthesis; (b) attaching a suture to at least one end portion of the tendon or ligament prosthesis; and (c) enclosing the prosthesis in a sterile package.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 7A is a schematic illustration of a tendon bioprosthesis illustrating tensile testing thereof with a failure site outside the bounds of the implanted construct.

FIG. 7B is a graph of tensile strength (Newtons) at 3 weeks post-implantation and at various locations for the construct shown in FIG. 7A.

FIG. 7C is a graph of tensile strength (Newtons) at 6 weeks post-implantation and at various locations for the construct shown in FIG. 7A.

FIG. 7D is a graph of tensile strength (Newtons) from 3 weeks to 48 weeks post-implantation with the construct of FIG. 7A and a contralateral control.

DETAILED DESCRIPTION

Figure 1A:
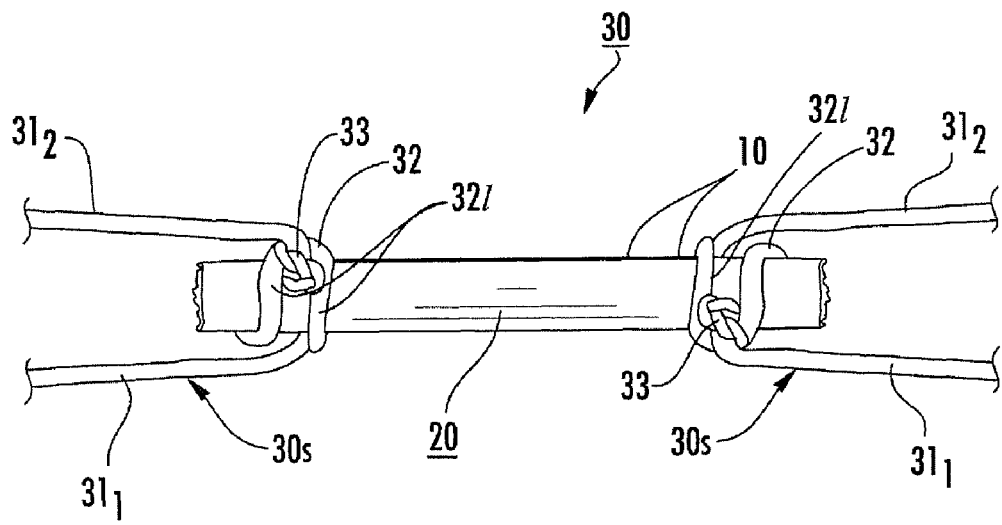
FIG. 1A is a top view of an array or bundle of fibers used to form an implantable biocompatible construct according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "implant" and "prosthesis" are used interchangeably herein to designate a product configured to repair or replace (at least a portion of) a natural tendon, ligament or other tissue of a mammalian subject (for veterinary or medical (human) applications). The term "implantable" means the device can be inserted, embedded, grafted or otherwise chronically attached or placed on or in a patient. The term "tissue" means skin, muscle, bone or other group of cells.

The term "array" means an arrangement of fibers in rows and/or columns that are held together as in a matrix.

Collagen "microfibrils," "fibrils," "fibers," and "natural fibers" refer to naturally-occurring structures found in a tendon. Microfibrils are about 3.5 to 50 nm in diameter. Fibrils are about 50 nm to 50 µm in diameter. Natural fibers are above 50 µm in diameter. A "synthetic fiber" refers to any fiber-like material that has been formed and/or chemically or physically created or altered from its naturally-occurring state. For example, an extruded fiber of fibrils formed from a digested tendon is a synthetic fiber but a tendon fiber newly harvested from a mammal is a natural fiber. Of course, synthetic collagen fibers can include non-collagenous components, such as particulates, hydroxyapatite and other mineral phases, or drugs that facilitate tissue growth. For example, the fibers and/or constructs formed from the fibers can include compositions can contain carbon nano-tubes, zinc nano-wires, nanocrystalline diamond, or other nano-scale particulates; larger crystalline and non-crystalline particulates such as calcium phosphate, calcium sulfate, and apatite minerals. For example, the compositions can contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, and decorin. See, e.g., U.S. Pat. No. 6,821,530, the contents of which are hereby incorporated by reference as if recited herein. In some embodiments, the constructs can contain cells, engineered cells, stem cells, and the like. Combinations of the above or other materials can be embedded, coated and/or otherwise attached to the construct.

The term "suture" refers to a flexible elongate material that is used to attach the bioprosthesis to a target anatomical structure to help hold the bioprosthesis in location in the body. The suture may be resorbable or non-resorbable, synthetic or natural. The suture can be configured to hold the implant in location for at least an initial post-implantation period of at least about 1 week, but may reside permanently in the body or, as noted above, may be substantially resorbable over time. The suture can be a single filament or multi-filament thread, floss, gut or wire, or combinations thereof that can be used to hold a portion of an implant against or attached to target structures, typically to bone and/or tissue. The suture may comprise a resorbable or non-resorbable biocompatible material. Examples of suture materials include elastomeric materials, such as, for example, polymers, copolymers and/or derivatives thereof, including Vicryl®, as well as other materials including, for example, NITINOL, and combinations thereof. The suture may be used with a suture anchor (bone or tissue anchor), staple, screw, plate or other biocompatible fixation member to affix the implant in the desired location and/or orientation.

The term "atraumatic" with respect to suture needles with thread refers to an atraumatic or eyeless needle attached to a specific length of suture material (thread or filament). The suture and needle are preformed and purchased as a unit, as the suture needle manufacturer swages or binds the suture thread to the eyeless atraumatic needle at the factory. In a conventional traumatic needle with suture, the thread comes out of the needle's hole or eye on both sides. When passing through the tissues, this type of suture may rip tissue, at least to a certain extent. In contrast to the conventional "trauma"-type needle with suture, the atraumatic needle with suture does not cause trauma (hence the name "atraumatic"). Because of these advantages, atraumatic needles with sutures are today very widely used.

As with conventional sutures, the sutures of atraumatic needles can be absorable or non-absorable. As is well known, there are several shapes of atraumatic needles, including straight, half curved, one-third curved and others. The body of the needle is available also in different makes, like circular, with edge on the outer side, with edge on the inner side, and others.

The term "flexible" means that the so-called member can be flexed or bent.

The array of fibers can be held together in any suitable manner including by their natural affinity to stick together upon compression or extrusion, by using a sticky coating or adhesive, such as a gelatinous coating, or by otherwise attaching the fibers to form the array. In some embodiments, the fibers can comprise polyglycolic acid, polylactice acid, or combinations of these, as discussed below, to help hold the fibers together for the bioprosthesis, such as, for example, an Achilles Tendon implant. The fibers may also optionally comprise braided segments. The term "braided" and derivatives thereof mean to (inter)weave and/or interlock in any manner, three or more fibers or bundles of fibers together, including knitting and knotting and combinations of these or other interlocking constructions.

FIG. 1A is a schematic illustration of an implantable construct 20 with multiple fibers 10 that can be held together to form an array of fibers 10a. As shown in FIG. 1A, the multiple fibers 10 can be axially arranged so that at least a majority of the fibers are substantially parallel to each other over at least a major portion of the length of the construct 20, typically over substantially the entire length of the construct 20. The construct 20 and/or fibers 10 can incorporate anti-inflammatory agents or other pharmaceutically suitable agents. The construct 20 and/or fibers 10 can be coated or impregnated with a thin film of polylactic acid (PLA) or other suitable substance to promote strength and/or ease of handling. For example, the construct 20 can be dipped, painted or sprayed with a 3% solution of PLA in chloroform or other suitable solution.

Figure 1B:
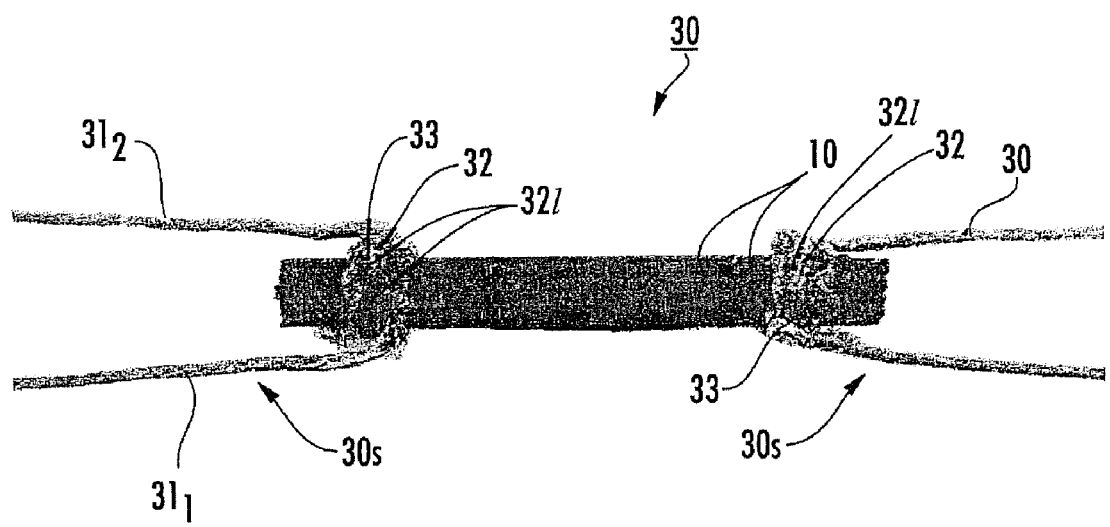
FIG. 1B is a digital photograph of a prototype of a biocompatible construct according to embodiments of the present invention.

FIG. 1A also illustrates that an attachment member 30, such as a suture 30s, can be attached to each end portion of the construct 20 and used to affix the construct 20 to local tissue. In the embodiment shown in FIGS. 1A and 1B, the suture 30s is tied to the construct 20 so that opposing legs $31_1$, $31_2$ that extend from a looped portion 32 of the suture have one or more loops 321 encasing the construct 20 that is tied to form one or more knots 33. The knot 33 can be configured to provide a secure attachment to the array or fiber bundle 20a and organize the parallel array of fibers into a desired cross-sectional configuration (see, e.g., FIGS. 2A, 2B). The knot configuration can position the suture $30_s$ to reach out into adjacent tissue for anchorage at about 180 to about 360 degrees from each other. The suture legs $31_1$, $31_2$ can extend substantially parallel to each other from opposing outer lateral edges of the construct 20 in the direction of the target anchoring-site. In the embodiment shown, the sutures 30s are oriented to exit the construct body outside the bounds of the construct itself at opposing side locations and extend substantially parallel to the anchoring site. The looped portion 32 and the knot(s) 33 are configured to improve tensile/compression force distribution and/or cancel unwanted torque. In some embodiments, the attachment member 30 (suture(s)) can be placed, e.g., tied to the implant/construct when the fibers are dry and the suture(s) can hydraulically fix in place when the bioprosthesis hydrates after placement in vivo. See, e.g., co-pending U.S. Provisional Application Ser. No. 60/890/679, the contents of which are hereby incorporated by reference as if recited in full herein.

In the embodiment shown in FIG. 1A, a multi-fiber bundle 20a has a knot configuration that is formed by a loop 32 around the bundle 20a secured by a square knot followed by additional loops each ending in two half-hitches. The number of additional loops 32 can be adjusted in accordance with the diameters of the suture material and the size of the fiber bundle 20a to facilitate the correct positioning of the exit legs or strands $31_1$, $31_2$. Other knot configurations may also be used. The number of fibers 10 used in the embodiment shown in FIG. 1A is sixteen (16), but greater or lesser numbers may also be used, typically depending on the target repair site.

In some embodiments, other initial knot configurations may be used in lieu of or with the square knot, although typically the first knot is tied to be substantially flat so as to not to unduly project and irritate local structure when implanted. Similarly, instead of or in combination with half-hitches, other knots can be used with the loops, and different loops may have different knot configurations or may even knot use a knot on a particular loop.

One intended use of the construct as a bioprosthesis is to bridge gaps in tendon and ligaments by providing the construct in a matching length and suturing into the patient's own remaining tendon or ligament end portions using a suitable surgical tying technique, such as, for example, but not limited to, a double Kessler technique or similar methodology.

Figure 1C:
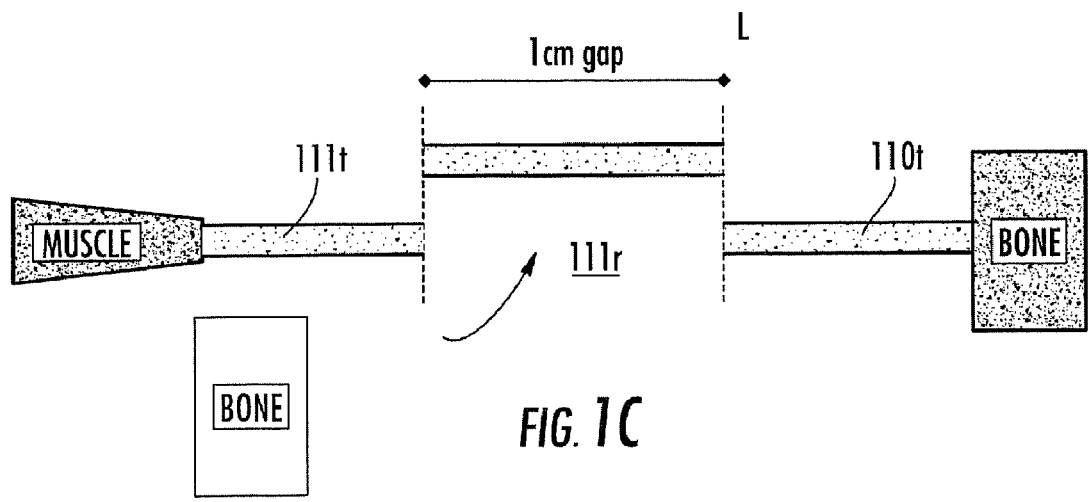
FIG. 1C is a schematic illustration of a target repair site.
Figure 1D:
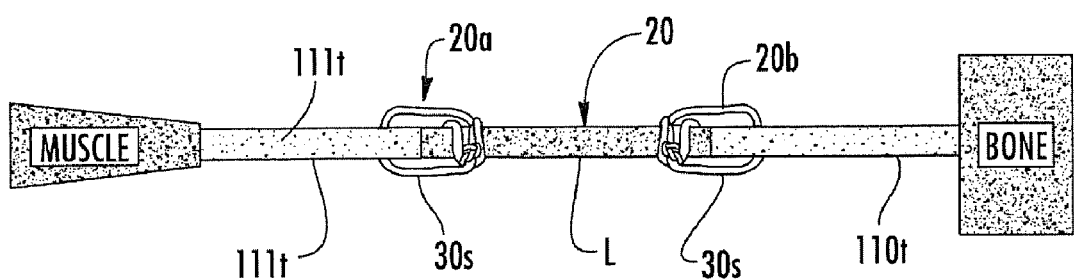
FIG. 1D is a schematic illustration of an implantable construct placed at the target repair site according to embodiments of the present invention.

FIG. 1C illustrates an example of a target repair site 111r with two separated tendon ends 111t, 110t that can be treated with the construct 20 implanted in the subject according to embodiments of the invention. As shown, the construct 20 is for an Achilles tendon repair. As shown in FIG. 1D, one end portion of the construct 20a is attached to the first separated portion of the tendon 110t undergoing repair and/or treatment and the other end portion 20b is attached to the spaced apart portion of the tendon 111t. As is also shown, the first end portion 20a is attached via a suture 30s and the second end portion 20b is attached using a suture 30s. Other anchoring or attachment means may be used. The sutures 30s may be resorbable or non-resorbable. Adhesive 22 may be used to help secure one or both of the end portions 20a, 20b during an initial healing phase for additional stabilization.

The construct 20 can be preformed in different lengths for selection by a clinician during a surgical procedure or can be cut to length in situ by a clinician. The construct 20 can be preformed with the suture(s) 30 attached to the construct and provided in a medical kit to reduce onsite preparation time. This embodiment may be particularly suitable where the construct 20 is provided in predetermined lengths. The construct 20 can be configured to have a strength and stiffness similar to natural tendon or ligament and can provide an effective scaffold for neo-tendon and ligament to grow into and further enhance the repair.

In some embodiments, the plurality of fibers 10 in a respective construct 20 can be between about six to about fifty, typically between about ten to about twenty-seven. Lesser and greater numbers of fibers may be used depending on the desired strength or other mechanical parameter of the target implant site.

Figures 2A, 2B:
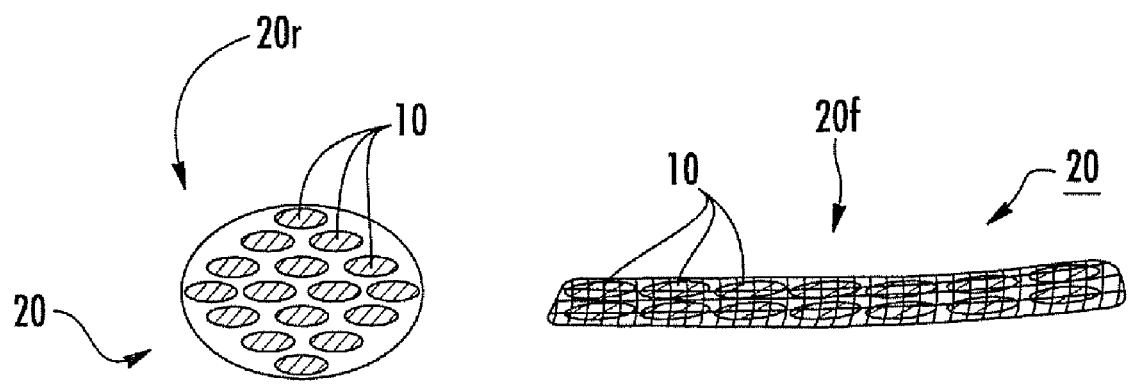
FIGS. 2A-2C are cross- and longitudinal-views of the implant shown in FIG. 1A illustrating exemplary configurations according to embodiments of the present invention.
Figure 2C:
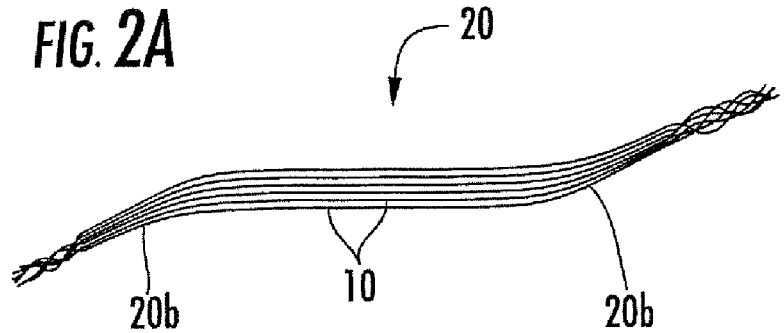

FIGS. 2A and 2B illustrate that the construct 20 can have different cross-sectional shapes. FIG. 2A illustrates that the construct can have a substantially tubular shape 20r, with a circular or oval cross-sectional shape, while FIG. 2B illustrates that the construct has a substantially flat configuration 20f. FIG. 2C illustrates that a portion of the construct 20 can include a braided segment 20b. As shown, the braided segment 20b is formed by bundles of the fibers in the array and may be used to provide a stronger attachment segment for a suture 30s or other attachment/fixation member 30. Combinations of these and other shapes over different portions of the body of the construct 20 may also be used. The construct 20f shown in FIG. 2B may be particularly suitable as a ligament prosthesis, such as for an ACL repair or replacement. The construct 20r shown in FIG. 2A may be particularly suitable as a tendon-prosthesis, such as, for example, the flexor tendon. Other configurations may also be used as suitable for the target treatment site/prosthesis.

Typically, the construct 20 is configured to have substantially the same physical thickness and/or configuration as the replaced or repaired tissue so as to not cause discomfort or physical abnormalities in structure.

The array can be a relatively tightly compressed array of fibers or a relatively loosely compressed or attached arrangement having voids between some adjacent fibers depending on the target location and the desired mechanical properties and configuration and to allow for neo tissue in-growth.

In some embodiments, the construct 20 is between about 0.5-50 cm long, typically between about 1-25 cm, and in some embodiments between about 1 cm to about 10 cm long. The construct 20 may have a width that is between about 0.05 to 8 cm, and is typically between about 1 cm-3 cm. The constructs 20 may have a cross-sectional thickness of about 0.01 to about 30 mm. For the flat construct 20f, the thickness may be more typically between about 0.1 to about 10 mm, while the tubular construct 20r may have a thicker cross-section, such as between about 5-30 mm.

Figure 3A:
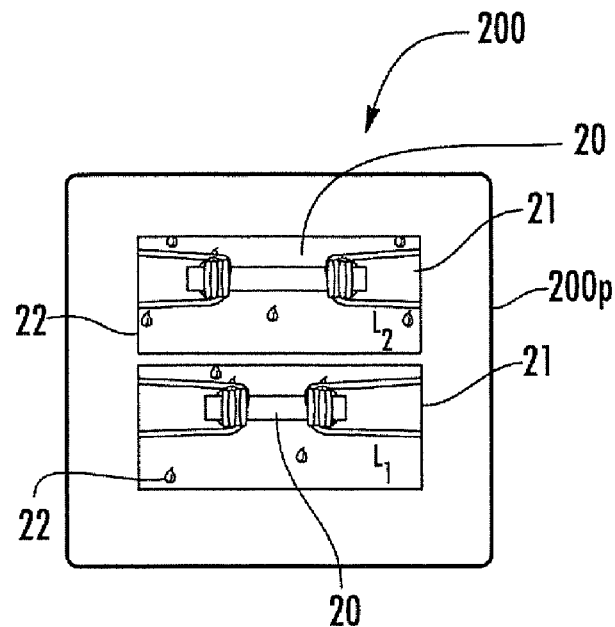
FIG. 3A is a schematic illustration of a medical kit according to embodiments of the present invention.

FIG. 3A illustrates a medical kit 200 that includes the braided construct 20 and may optionally include at least one suture 30s, which, as shown, may be pre-attached. The suture 30s may be provided in the form of an atraumatic needle with suture (not shown). The suture 21 can be a bone anchor suture and/or be configured to cooperate with a bone tunnel as is well-known. The kit 200 may include other components, such as, for example, a container of surgical adhesive and the like.

Figure 3B:
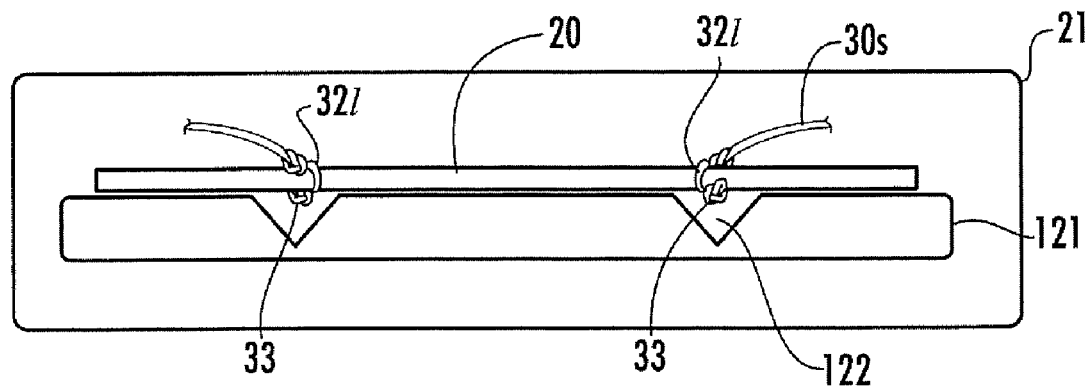
FIG. 3B is a schematic illustration of a medical kit with a substrate configured to hold the construct with suture(s) according to embodiments of the present invention.

The construct 20 may be held hydrated in a sterile flexible sealed package 21 of sterile liquid 22. The kit 200 may have a package 200p that can include more than one size (length and/or thickness) construct 20, shown as provided in two lengths, $L_1$, $L_2$. The kit 200 may include a temperature warning so that the construct 20 is not exposed to unduly hot temperatures that may degrade the implant. A temperature sensor may optionally be included on the package of the kit (not shown) to alert the clinician as to any excessive or undue temperature exposure prior to implantation. FIG. 3B illustrates the kit 200 can include a substrate that holds the construct 20 with a notch or well region to hold the loop/knot 32, 33 to maintain a desired orientation for easy-access to the construct 20 and suture(s) 30 at a point of use. The package 200 may also include a mating top or "lid" to trap the construct in position and/or protect it during shipment (not shown).

Figure 4:
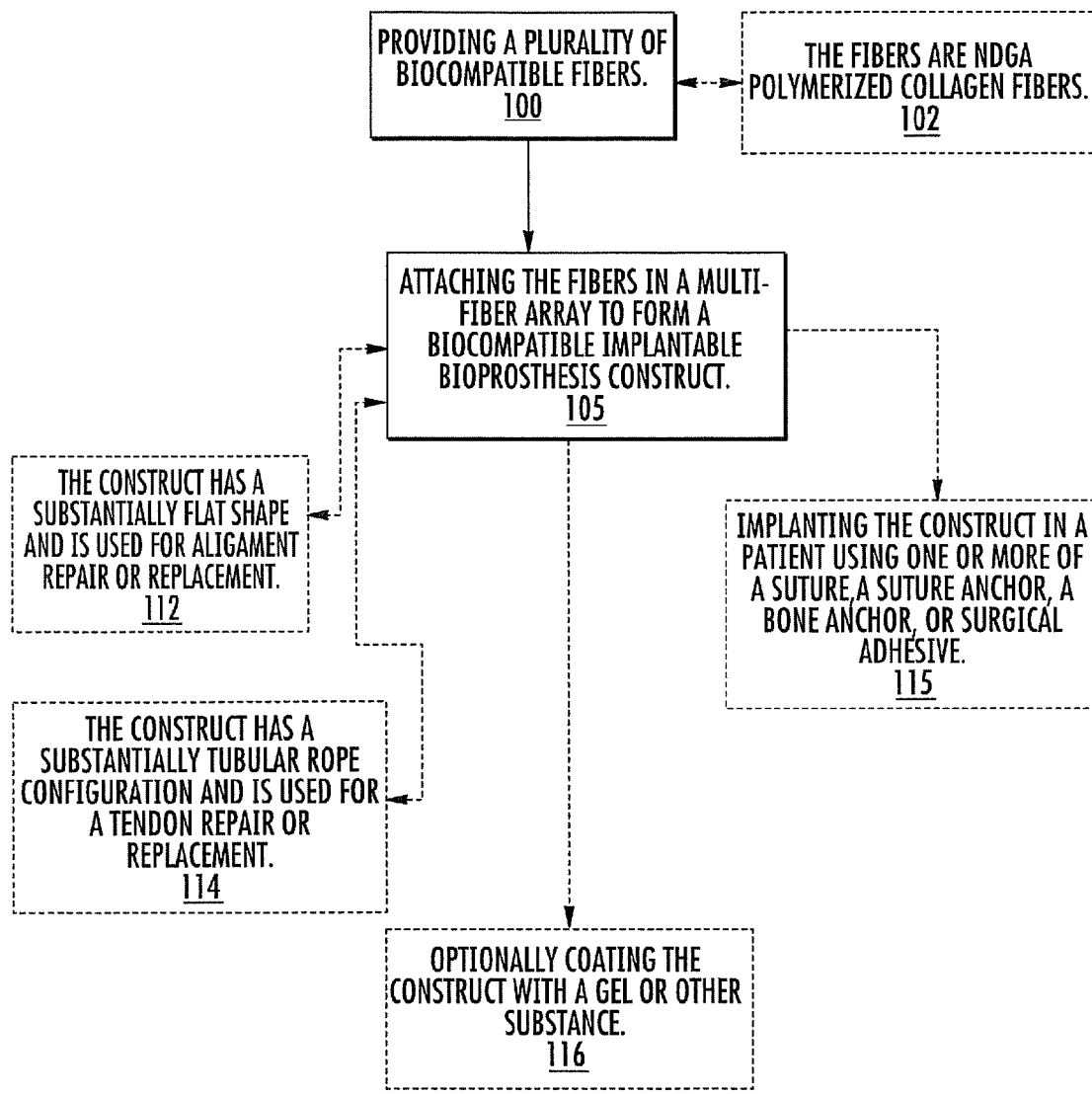
FIG. 4 is a flow chart of operations that can be used to carry out embodiments of the invention.

FIG. 4 illustrates some operations that can be used to carry out embodiments of the invention. As shown, a plurality of biocompatible fibers are provided (block 100). The fibers are attached as a multi-fiber array to form a biocompatible implantable bioprosthesis construct (block 110).

The fibers may comprise NDGA polymerized collagen fibers (block 102). The construct can have a flat shape and may be used for a ligament repair or replacement (block 112). The construct can have a substantially solid core tubular configuration or substantially circular cross-section and can be used for a tendon repair or replacement (block 114).

Optionally, the construct can be implanted in a patient using one or more of a suture, suture anchor, bone anchor, bone tunnel and the like (block 115). The suture can be a suture with an atraumatic needle and may be pre-applied to the construct and packaged in a medical kit for subsequent use.

Also, the construct can optionally include, e.g., be coated, impregnated and/or amalgamated with a gel or other material (block 116). The coating may be to promote fibroblasts, and/or comprise one or more of an anti-inflammatory agent, an antibiotic or other therapeutic agent.

The construct 20 is biocompatible and may be absorbed, resorbed and/or biodegradable over time.

The constructs 20 can be configured to have at least about 60% of the tensile strength of natural tendon, and may have tensile strength, and/or dynamic flexibility stiffness of similar to or even greater than these properties in corresponding natural tissue, e.g., natural ligament or tendon fibers. Embodiments of the invention may be particularly suitable for augmenting, repairing or replacing tendons and ligaments.

In some embodiments, the fibers comprise any collagen fibers formed in any suitable manner to be acceptable as a biomedical implant/construct.

In particular embodiments, the fibers can comprise NDGA-treated collagen. Suitable ways of forming NDGA polymerized and/or treated fibers are described in U.S. Pat. Nos. 6,565,960 and 6,821,530, the contents of which are hereby incorporated by reference as if recited in full herein. Generally stated, bulk collagen can be solubilized by digestion with a protease, then extruded into a synthetic fiber. Properly processed NDGA polymerized fibers are biocompatible. After the polymerization process, the fibers can be washed in ethanol and phosphate buffered saline to remove cytotoxins due to leachable reaction products.

Figure 5A:
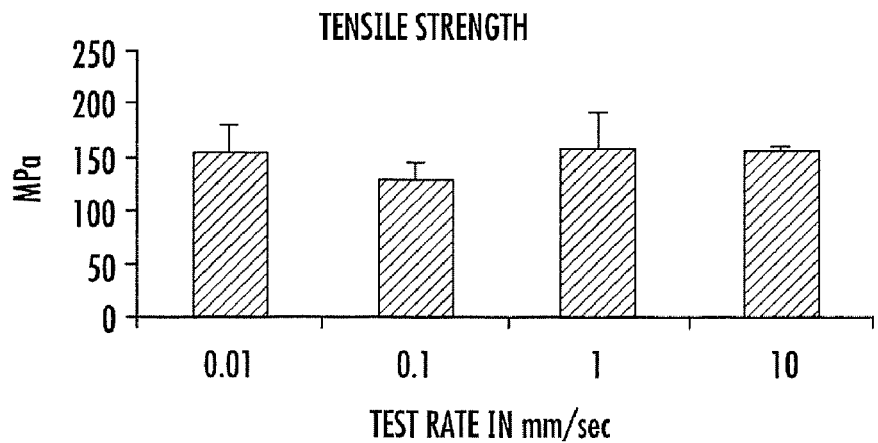
FIG. 5A is a graph of tensile strength of NDGA fibers of different fibers showing strength (MPa) as a function of test rate in mm/sec.
Figure 5B:
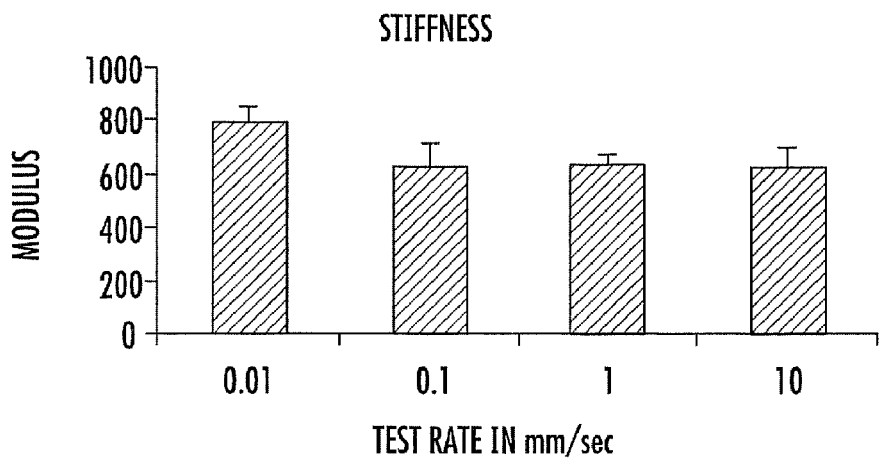
FIG. 5B is a graph of stiffness of NDGA fibers of different fibers showing modulus as a function of test rate in mm/sec.
Figure 5C:
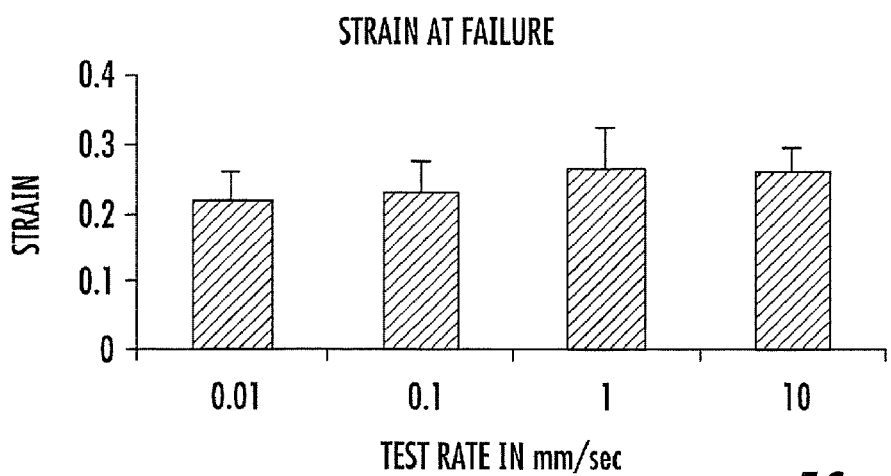
FIG. 5C is a graph of strain at failure of NDGA fibers of different fibers showing strain as a function of test rate in mm/sec.

Testing has been demonstrated that NDGA-treated collagen fibers are biocompatible and have desirable mechanical properties. FIGS. 5A-5C illustrate exemplary strain rates of NDGA treated collagen fibers. The fibers were mounted in clamps with 2 cm nominal tested length. Fibers were deformed to failure. As shown, the fibers are nearly elastic in tension; i.e., strain rate independent. The linear portion of the stress/strain curve was used to calculate the elastic modulus (stiffness) and the force at which the fibers failed was normalized to cross sectional area yielding tensile strength. Values shown are means+/−S.D. for six specimens. For additional discussion of the NDGA polymerized fibers, see, Thomas J. Koob, *Biomimetic approaches to Tendon Repair*, Comparative Biochemistry and Physiology Part A 133 (2002) 1171-1192. See also, co-pending U.S. Provisional Application Ser. No. 60/883,408, filed Jan. 4, 2007 to Koob et al., entitled, Methods of Making High Strength NDGA Polymerized Collagen Fibers and Related Collagen-Prep Methods, Medical Devices and Constructs, the contents of which are hereby incorporated by reference as if recited in full herein.

In some embodiments, the NDGA collagen fibers may, in some embodiments, be high-strength. The term "high-strength" refers to fibers having an average tensile strength of at least about 150 MPa, such as between about 180 MPa and 350 MPa, and typically, for bovine, porcine or caprine based "donor" collagen, between about 180 MPa and 280 MPa, such as between about 240-279 MPa (measured on average). The fibers may also have suitable stiffness and strain yield. In general, the fibers can have a stiffness of at least about 200 MPa (e.g., at least about 300, 400, 500, or 600 MPa), and a strain at failure of less than about 20% (e.g., less than about 15 or 10%). The fibers may be formed with a relatively thin diameter, such as, for example about a 0.08 mm dry diameter (on average) and about a 0.13 mm wet diameter (on average).

To make the collagen fibers, preparatory donor collagen material can be pepsin-derived or solubilized collagen that is processed/purified. The purified collagen preparatory material is dialyzed a plurality of times in a selected liquid for a desired period of time. The dialyzing is typically repeated three times. The dialyzing can be carried out against dionized (DI) water in a volume ratio of between about 30:1 to about 100:1, typically about 60 to 1, for between about 30-90 minutes, typically about 40 minutes. The dialyzing can form a substantially clear gel of collagen fibrils indicating good organization (substantially parallel fibrils), where opacity indicates less organization. The organization can help improve tensile strength of subsequently cross-linked fibers.

The dialyzed collagen material can be incubated for a desired time before placing in a fiber-forming buffer. The dialyzed gel can be cross-linked to provide collagen fibers for medical constructs. The polymerization (e.g., cross-linking) can be carried out using NDGA and the resultant NDGA treated collagen fibers can be relatively thin, such as, for example, about 0.08 mm dry diameter (on average).

The incubation may be for at least about 24 hours, typically 24-48 hours, and may be at room temperature of between about 15-30° C., typically about 25° C. The dialysis process can be used before cross-linking for subsequent use with any suitable cross-linking materials, to promote collagen organization, such as, for example, and the process is not limited to NDGA, but may be useful with other materials, including, for example, glutaraldehyde.

For additional discussion of methods used to form high-strength NDGA treated collagen fibers, see, U.S. Provisional Application Ser. No. 60/883,408 and/or its corresponding regular utility counterpart, the contents of which are incorporated by reference herein.

The array or bundle 20 can be formed with fibers having widths in any suitable range, typically in the range of between about 0.01-10 mm. One or more of the fibers 10 may be continuous or discontinuous over the length of the construct 20.

The present invention is explained in greater detail in the following non-limiting Examples.

EXAMPLES

Tendon replacement was performed in rabbit Achilles tendon using a parallel array of fibers tied together with a knot made of suture material. The fibers were made from NDGA cross-linked collagen as described above and in U.S. Pat. No. 6,565,960. In-vivo studies were conducted using the rabbit model, wherein a 1 cm gap in the gastrocnemius tendon was replaced with a 16 fiber 1 cm long bioprosthesis (Vicryl 4-0 sutures). The results showed excellent biocompatibility, abundant formation of neo-tendon (FIGS. 6A, 6B) and biomechanical properties reaching 60% of the contralateral normal tendon with 6 weeks (FIG. 7C).

The Vicryl® suture used a knot that provided a secure attachment to the bundle and organized the parallel array of fibers into a round cross section. Also, the knot positioned the sutures that reach out into the adjacent tissue anchorage at 180 degree to each other in order to cancel out unwanted torque. The knot configuration had a loop around the bundle secured by a square knot followed by additional loops each ending in two half hitches.

Figure 6A:
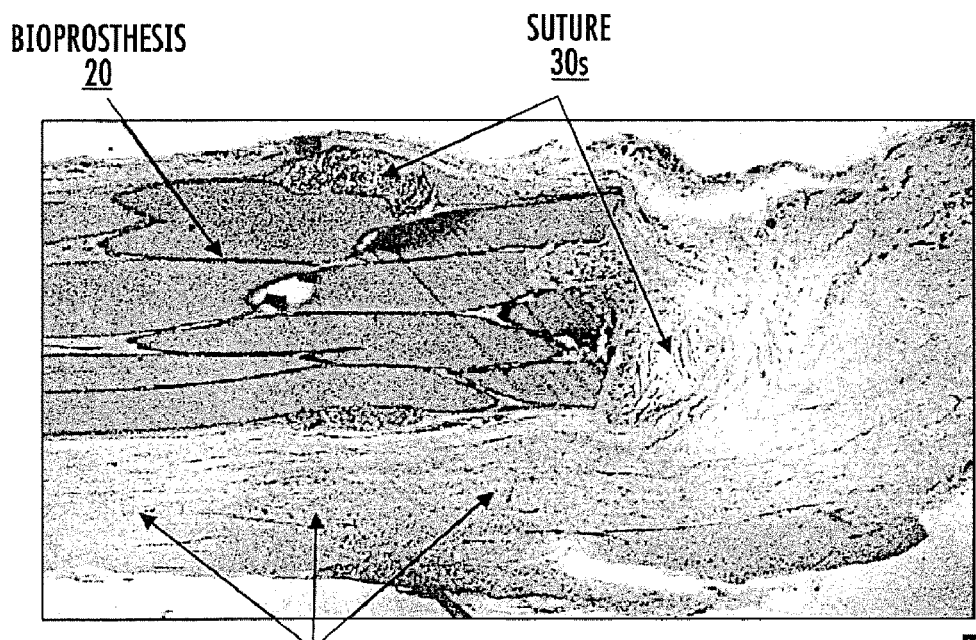
FIG. 6A is an enlarged digital photograph of an implanted construct illustrating the construct and suture with neo-tendon growth based on in vivo trials.
Figure 6B:
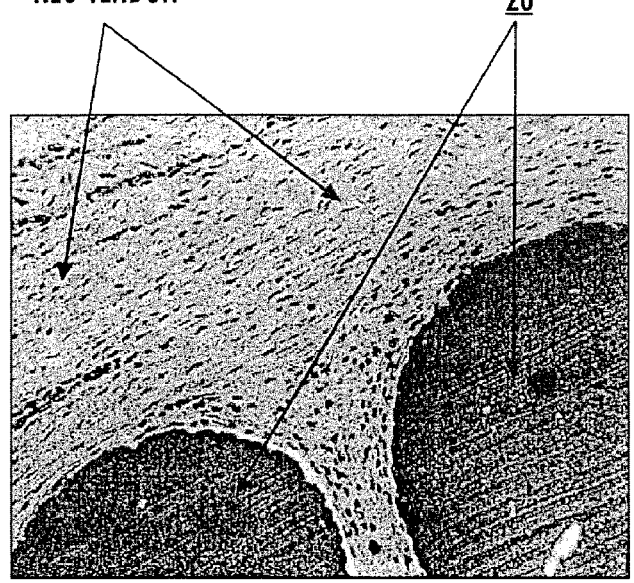
FIG. 6B is a greatly enlarged digital photograph of the implanted construct shown in FIG. 6A illustrating a sectional view of fibers and neo-tendon growth.

FIG. 6A is an enlarged digital photograph of an implanted construct illustrating the construct and suture with neo-tendon growth based on the in vivo rabbit trials. FIG. 6B is a greatly enlarged digital photograph of the implanted construct shown in FIG. 6A illustrating a sectional view of fibers and neo-tendon growth.

FIG. 7A is a schematic illustration of a tendon bioprosthesis illustrating tensile testing thereof with a failure site outside the bounds of the implanted construct. FIG. 7B is a graph of tensile strength (Newtons) at 3 weeks post-implantation and at various locations for the construct shown in FIG. 7A. FIG. 7C is a graph of tensile strength (Newtons) at 6 weeks post-implantation and at various locations for the construct shown in FIG. 7A. FIG. 7D illustrates additional tensile strength data on ex vivo mechanical tests out to 48 weeks (of the bioprosthesis repair using a construct shown in FIG. 7A and a contralateral control).

This bioprosthesis offers the advantages of having strength and stiffness similar to natural tendon or ligament, excellent biocompatibility, and provides an effective scaffold for neo-tendon and ligament to grow in and further enhance the repair.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. An implantable ligament or tendon bioprosthesis, comprising:
   a flexible implantable biocompatible construct comprising polymerized collagen fibers having opposing first and second end portions, wherein the construct is configured as an array of substantially parallel polymerized synthetic collagen fibers;
   a first suture wrapped laterally at least once about a perimeter of the first end portion of the construct and tied with a first square knot; and a second suture wrapped laterally at least once about the perimeter of the second end portion of the construct and tied with a second square knot, wherein each suture has a pair of suture legs that extend away from the respective square knot for affixing the construct to local bone or tissue, and wherein the sutures are resorbable and adapted to anchor to local tendon or ligament structure, wherein each of the first and second sutures are further wrapped around the respective end portion of the flexible construct and further tied with a respective pair of half-hitch knots such that each respective pair resides substantially symmetrically across from each other on opposing lateral sides of the construct so that the pairs of the suture legs both extend axially away from the construct from a respective exit location that is laterally outside the bounds of the construct, and wherein one leg in each pair is transversely spaced apart from the other so that a first leg in each pair extends axially away from the construct adjacent a first long side of the construct and a second leg in each pair extends axially away from the construct adjacent an opposing second long side to attach to local tendon or ligament structure.

2. A bioprosthesis according to claim 1, wherein the fibers are NDGA polymerized collagen fibers.

3. A bioprosthesis according to claim 1, wherein at least one of the sutures is wrapped a second and third time with respective second and third loops of the suture, and wherein each of the second and third loops end with an additional pair of half hitch knots oriented to provide a desired exit configuration of the suture legs.

4. A bioprosthesis according to claim 2, wherein the construct of substantially parallel NDGA polymerized collagen fibers has between about 15-57 elongate synthetic fibers compressed together so that adjacent fibers snugly contact each other over at least a major portion of a length of the construct to define the construct.

5. A bioprosthesis according to claim 1, wherein the construct comprises a gelatinous coating.

6. A bioprosthesis according to claim 1, wherein the construct comprises a thin film polylactic acid coating formed by a 3% solution of the polylactic acid.

7. A bioprosthesis according to claim 1, wherein the sutures are 4-0 resorbable sutures.

8. A bioprosthesis according to claim 1, wherein the polymerized fibers are NDGA polymerized collagen fibers, and wherein there is abundant formation of neo-tendon or ligament into the construct at six weeks post-implantation as measured in a rabbit Achilles tendon model, and wherein the NDGA polymerized collagen fibers having an average tensile strength between about 180 MPa and 350 MPa, a stiffness of at least about 200 MPa, and a strain at failure of less than about 20%.

9. A bioprosthesis according to claim 8, wherein tensile strength of the construct is at least about 60% of a contralateral normal tendon at 6 weeks.

10. A bioprosthesis according to claim 1, wherein the construct is between about 1 cm-5 cm long, and wherein the fibers have a diameter of between about 0.01 mm to about 10 mm.

11. A bioprosthesis according to claim 8, wherein the construct is between about 0.1 cm to 5 cm wide.

12. A bioprosthesis according to claim 2, wherein the construct has a substantially flat configuration sized and configured to define a ligament bioprosthesis.

13. A bioprosthesis according to claim 12, wherein the ligament bioprosthesis is an ACL bioprosthesis.

14. A bioprosthesis according to claim 2, wherein the construct has a substantially circular cross-sectional configuration sized and configured to define a tendon bioprosthesis.

15. A bioprosthesis according to claim 14, wherein the tendon bioprosthesis is a flexor tendon bioprosthesis.

16. A bioprosthesis according to claim 12, wherein the construct has a tensile strength, stiffness and dynamic flexibility that meets at least 60% that of a pre-injury natural ligament undergoing treatment after 6 weeks.

17. A bioprosthesis according to claim 14, wherein the construct has a tensile strength, stiffness and dynamic flexibility that meets at least about 60% of a pre-injury natural tendon undergoing treatment after 6 weeks.

18. An implantable ligament or tendon bioprosthesis, comprising:
a flexible implantable biocompatible construct having a primary body comprising an array of substantially parallel polymerized collagen fibers having opposing first and second end portions, with at least one of the end portions merging into a braided segment of bundles of fibers defining the array; and
a first suture pre-attached to the first end portion of the construct and a second suture pre-attached to the second end portion of the construct, wherein each of the first and second sutures are attached to the construct with a respective square knot and at least one respective pair of half-hitch knots,
wherein each suture has a pair of suture legs that extend away from the respective square knot, wherein the half-hitch knots of each respective pair reside substantially symmetrically across from each other on opposing lateral sides of the construct so that the pairs of suture legs both extend axially away from the construct from a respective exit location that is laterally outside the bounds of the construct, and wherein one leg in each pair is transversely spaced apart from the other so that a first leg in each pair extends axially away from the construct adjacent a first long side of the construct and a second leg in each pair extends axially away from the construct adjacent an opposing second long side to attach to local tendon or ligament structure.

19. A medical kit for a tendon or ligament repair, augmentation or replacement, comprising:
an implantable bioprosthesis construct having a primary body defined by an array of substantially parallel NDGA collagen fibers and having at least one suture attached to at least one end portion thereof, wherein the at least one suture comprises a first suture that is attached to an outer surface of the construct with a square knot, the square knot merging into a pair of longitudinally extending free legs, wherein the free legs proximate the square knot are transversely spaced apart from each other; and
a sterile package sealably enclosing the collagen fiber construct with the at least one suture attached therein,
wherein the first suture is wrapped around the at least one end portion of the construct and further tied with a pair of half-hitch knots that reside substantially symmetrically across from each other on opposing lateral sides of the construct so that the pair of free legs extends axially away from the construct from a respective exit location that is laterally outside the bounds of the construct, and wherein one leg in the pair is transversely spaced apart from the other so that a first leg in the pair extends axially away from the construct adjacent a first long side of the construct and a second leg in the pair extends axially away from the construct adjacent an opposing second long side to attach to local tendon or ligament structure.

20. A medical kit according to claim 19, wherein the construct has a substantially flat configuration.

21. A medical kit according to claim 19, wherein the construct is a bioprosthesis ligament for a ligament repair, augmentation or replacement.

22. A medical kit according to claim 19, wherein the construct has a substantially circular configuration and is a bioprosthesis for a tendon repair, augmentation or replacement.

23. A bioprosthesis according to claim 1, wherein the sutures are pre-attached to the construct with the respective square knots and half-hitch knots and provided as an assembled construct ready for implantation.

24. A medical kit according to claim 19, wherein the at least one suture comprises the first suture and a second suture, the first suture square knot is attached to a first end portion of the construct and the second suture is attached to an opposing second end portion of the construct, the second suture comprises a second square knot residing on the outer surface of the construct that merges into a second pair of longitudinally extending free legs, and wherein the first and second sutures are provided with the construct in the package in a pre-attached configuration.

25. A medical kit according to claim 19, further comprising a substrate with a notch or well region holding the suture knot to provide a desired orientation of the suture and construct.

26. A medical kit with an implantable ligament or tendon bioprosthesis, comprising:
a sterile package;
a flexible elongate implantable biocompatible construct in the package, the construct comprising NDGA polymerized collagen fibers having opposing first and second end portions; and
a first suture pre-attached to the first end portion of the construct and a second suture pre-attached to the second end portion of the construct, wherein each of the first and second sutures are attached to the construct with a respective square knot and at least one respective pair of half-hitch knots,
wherein each suture has a pair of suture legs that extend away from the respective square knot, wherein the half-hitch knots of each respective pair reside substantially symmetrically across from each other on opposing lateral sides of the construct so that the pairs of suture legs both extend axially away from the construct from a respective exit location that is laterally outside the bounds of the construct, and wherein one leg in each pair is transversely spaced apart from the other so that a first leg in each pair extends axially away from the construct adjacent a first long side of the construct and a second leg in each pair extends axially away from the construct adjacent an opposing second long side to attach to local tendon or ligament structure.

27. A medical kit according to claim 26, further comprising a substrate in the sterile package holding the construct with the first and second sutures, the substrate comprising notches or wells configured to receive the suture knots.

28. A medical kit according to claim 25, wherein the substrate has a planar open upper surface that holds the implant with the notches or wells spaced apart on opposing end portions thereof to releasably hold the respective suture knots.

29. A medical kit according to claim 27, wherein the substrate has a planar open upper surface that holds the implant with the notches or wells spaced apart on opposing end portions thereof to releasably hold the respective suture knots.

30. A medical kit according to claim 19, wherein the first suture is wrapped a second and third time with respective second and third loops of the suture, and wherein each of the second and third loops end with an additional pair of half hitch knots oriented to provide a desired exit configuration of the suture legs.

31. A medical kit according to claim 30, wherein the construct of substantially parallel NDGA polymerized collagen fibers has between about 15-57 elongate NDGA polymerized collagen fibers compressed together so that adjacent fibers snugly contact each other over at least a major portion of a length of the construct to define the construct.

\* \* \* \* \*